United States Patent
Tsai et al.

(10) Patent No.: US 10,401,264 B2
(45) Date of Patent: Sep. 3, 2019

(54) EFFICIENT ELECTROSTATIC PARTICLE-INTO-LIQUID SAMPLER WHICH PREVENTS SAMPLING ARTIFACTS

(71) Applicant: National Chiao Tung University, Hsinchu (TW)

(72) Inventors: Chuen-Jinn Tsai, Hsinchu County (TW); Chao-Ting Hsu, Taichung (TW)

(73) Assignee: NATIONAL CHIAO TUNG UNIVERSITY, Hsinchu (TW)

( * ) Notice: Subject to any disclaimer, the term of this patent is extended or adjusted under 35 U.S.C. 154(b) by 260 days.

(21) Appl. No.: 15/671,405

(22) Filed: Aug. 8, 2017

(65) Prior Publication Data

US 2019/0049345 A1     Feb. 14, 2019

(51) Int. Cl.
  *G01N 1/22*     (2006.01)
  *G01N 1/38*     (2006.01)

(52) U.S. Cl.
  CPC ............ *G01N 1/2214* (2013.01); *G01N 1/38* (2013.01); *G01N 2001/2223* (2013.01); *G01N 2001/383* (2013.01)

(58) Field of Classification Search
  CPC ................... G01N 1/2214; G01N 1/38; G01N 2001/2223; G01N 2001/383
  See application file for complete search history.

(56) References Cited

U.S. PATENT DOCUMENTS

| | | | | |
|---|---|---|---|---|
| 3,414,238 A | * | 12/1968 | Catanzaro | G01N 1/38 366/131 |
| 3,588,053 A | * | 6/1971 | Rothermel | B01F 5/0057 366/131 |
| 3,754,868 A | * | 8/1973 | Witz | G01N 1/2202 422/52 |
| 5,914,454 A | * | 6/1999 | Imbaro | B01D 53/1418 261/79.2 |
| 6,484,594 B1 | * | 11/2002 | Saaski | G01N 1/2273 73/863.21 |
| 6,508,864 B2 | * | 1/2003 | Day | B01D 45/12 95/219 |
| 6,688,187 B1 | * | 2/2004 | Masquelier | G01N 1/2214 73/863.22 |
| 6,955,075 B2 | * | 10/2005 | Carlson | B03C 3/32 73/28.02 |
| 7,631,567 B1 | * | 12/2009 | Hill | G01N 1/2202 73/863.22 |

(Continued)

*Primary Examiner* — David J Bolduc
(74) *Attorney, Agent, or Firm* — Muncy, Geissler, Olds & Lowe, P.C.

(57) ABSTRACT

The present invention discloses an efficient electrostatic particle-into-liquid sampler (EPILS). The EPILS collects an aerosol sample in the dry mode and extracts it in the wet mode to prevent sampling artifacts. In the dry mode, a first stage utilizes carbon brushes as discharge electrodes to charge aerosol particles which are then collected on the cylinder wall by the electric field setup between the high-voltage central metal rod and the grounded cylinder in the second stage. In the wet mode, DI water is injected into the EPILS in a pulsation manner by opening and closing solenoid valves intermittently, which dislodges aerosol particles deposited on the cylinder wall effectively to become a liquid aerosol sample. The liquid aerosol sample is then analyzed for chemical compositions manually or automatically.

6 Claims, 4 Drawing Sheets

(56) References Cited

U.S. PATENT DOCUMENTS

| | | | | |
|---|---|---|---|---|
| 7,767,150 B1* | 8/2010 | Zaromb | | G01N 1/2202 422/400 |
| 9,671,320 B2 | 6/2017 | Yang et al. | | |
| 2002/0018211 A1* | 2/2002 | Megerle | | G01N 15/14 356/440 |
| 2003/0136205 A1* | 7/2003 | Totoki | | B01D 49/00 73/864.71 |
| 2003/0226391 A1* | 12/2003 | Sanderson | | G01N 1/2208 73/1.36 |
| 2004/0069047 A1* | 4/2004 | Coyle | | B01D 50/004 73/28.04 |
| 2005/0156118 A1* | 7/2005 | Chua | | B01D 46/442 250/426 |
| 2005/0274206 A1* | 12/2005 | Coyle | | G01N 1/2208 73/864.71 |
| 2006/0016728 A1* | 1/2006 | Shorts | | B01D 45/12 209/1 |
| 2006/0110818 A1* | 5/2006 | Hill | | G01N 1/2202 435/287.1 |
| 2006/0123752 A1* | 6/2006 | Symonds | | B01D 45/16 55/434.2 |
| 2007/0113685 A1* | 5/2007 | Zaromb | | G01N 1/2214 73/863.21 |
| 2007/0193373 A1* | 8/2007 | Xie | | B01F 5/0682 73/863.03 |
| 2009/0139399 A1* | 6/2009 | Kang | | B01D 45/12 95/24 |
| 2010/0000943 A1* | 1/2010 | Carson | | B01D 1/0094 210/638 |
| 2010/0186524 A1* | 7/2010 | Ariessohn | | G01N 1/2202 73/863.22 |
| 2012/0045752 A1* | 2/2012 | Ensor | | B82Y 15/00 435/5 |
| 2012/0174650 A1* | 7/2012 | Ariessohn | | B08B 3/12 73/23.2 |
| 2012/0255861 A1* | 10/2012 | Hering | | G01N 1/2208 204/453 |
| 2014/0020558 A1* | 1/2014 | Gururaja Rao | | B01D 45/12 95/69 |
| 2014/0151543 A1* | 6/2014 | Nagano | | G01N 1/2214 250/282 |
| 2014/0238106 A1* | 8/2014 | Kashima | | G01N 1/2202 73/23.2 |
| 2014/0272935 A1* | 9/2014 | Dirckx | | G01N 1/38 435/5 |
| 2014/0339415 A1* | 11/2014 | Caldow | | G01N 27/624 250/281 |
| 2015/0233796 A1* | 8/2015 | Kashima | | H01J 49/0422 250/288 |
| 2017/0052094 A1* | 2/2017 | Yang | | G01N 1/2202 |

* cited by examiner

EFFICIENT ELECTROSTATIC PARTICLE-INTO-LIQUID SAMPLER WHICH PREVENTS SAMPLING ARTIFACTS

BACKGROUND OF THE INVENTION

Field of the Invention

The present invention relates generally to a sampler, and more particularly to an electrostatic particle-into-liquid (EP-ILS) sampler which collects an aerosol sample in a dry mode and extracts it into a liquid aerosol sample in a wet mode.

Description of the Prior Art $PM_{2.5}$ air quality and chemical composition will fluctuate with the changes in meteorological conditions and pollution sources. Conventionally, it relies on manual sampling and analysis to monitor $PM_{2.5}$ in the air. It leads to the defect that only daily average concentrations can be acquired. Hourly fluctuation of pollutants in the air cannot be observed using the conventional method.

Some commercially available instruments such as MAGRA, IGAC or AIM, which are based on the SJAC (steam-jet aerosol collector) and PILS (particle-into-liquid sampler), are used for determining the concentrations of inorganic soluble ions. Due to the application of high temperature vapor, previous studies have indicated that these sampling systems underestimate the concentrations of precursor gases ($NH_3$ and $SO_2$) and some ion species ($Na^+$, $NH_4^+$, $Cl^-$, $NO_3^-$, and $SO_4^{2-}$) comparing to those of the standard method.

U.S. Pat. No. 9,671,320 discloses a semi-dry type electrostatic cyclone sampler to collect charged particles with the help of the corona discharge and electric field in a dry mode and dislodges the collected particles in a wet mode when the corona discharge is turned off. However, the collecting surface for the particles is also the grounded electrode for the corona discharge. The particles collected on the surface will increase the resistance of the corona discharge and lower the current thereof, which will lead to reduction in particle collection efficiency. Besides, aerosol is introduced into the charging chamber in a tangential direction of its cylinder wall so that the aerosol flows in the chamber in the spiral manner. The particles in the spirally-flowing aerosol have higher chance to collide the discharge electrode or to attach to surfaces other than the desired collecting surface. Sampling artifacts are thus occurred.

Besides, to ensure higher collecting efficiency, the sampler disclosed in U.S. Pat. No. 9,671,320 needs to be operated at higher working voltage, which can easily lead to higher radicals and ozone concentrations. The radicals and ozone further lead to high background concentrations of $NH_4^+$ and $NO_3^-$ and thus causes sampling artifacts in later analysis.

SUMMARY OF THE INVENTION

One object of the present invention is to provide a sampler which can achieve high collection efficiency and low sampling artifact.

To achieve the above and other objects, the present invention provides an efficient electrostatic particle-into-liquid sampler, which includes a main body, a discharge electrode and a conductive rod. The main body has an aerosol inlet on a top side, an aerosol outlet on a bottom side, a water outlet on the bottom side, a cylinder wall and at least one water injecting opening formed on the cylinder wall. The cylinder wall defines a particle charging area communicating with the aerosol inlet. The cylinder wall also defines a particle collecting area communicating with the aerosol outlet. The water injecting opening is communicated with the particle charging area. The particle collecting area is communicated with and located downstream of the particle charging area. The cylinder wall is made of conductive material. The discharge electrode is disposed in the particle charging area and located below the aerosol inlet. The discharge electrode has at least one carbon fiber brush for corona discharge. The carbon fiber brush has a plurality of carbon fiber strips. The conductive rod is disposed in the particle collecting area for forming an electric field between the conductive rod and the cylinder wall in a manner that at least a part of charged particles could be deposited on the cylinder wall. After the high voltage of the discharge electrodes is turned off and the corona discharge is stopped, deionized water is injected into in the main body through the water inlet opening on the wall in the tangential direction in a pulsation manner by opening and closing solenoid valves intermittently to dislodge the particles deposited on the cylinder wall. The water outlet is adapted to sample the water. Ozone generated when the discharge electrode and the conductive rod are working is lower than 100 ppb.

The main body of the present invention is divided into a particle charging area and a particle collecting area so that most of particles can be collected in the particle collecting area. This two stage design enables lower working voltage for the fine carbon brushes discharge electrode to discharge corona. Therefore, the concentrations of generated ozone and radicals are reduced such that $NH_4^+$ and $NO_3^-$ sampling artifacts can thus be lowered.

DETAILED DESCRIPTION OF THE PREFERRED EMBODIMENTS

Figure 1:
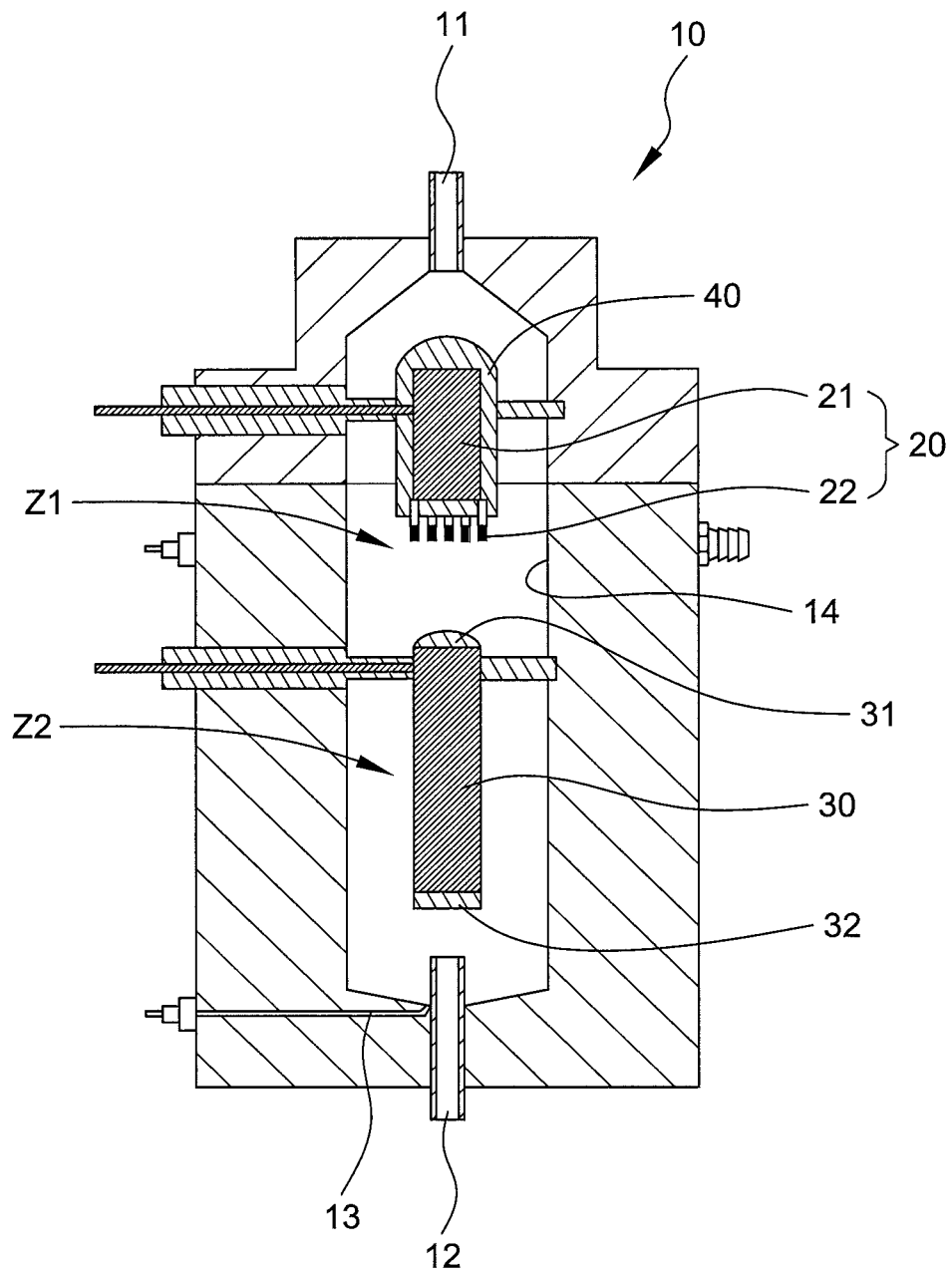
FIG. 1 is a longitudinal profile showing an embodiment of the present invention.
Figure 2:
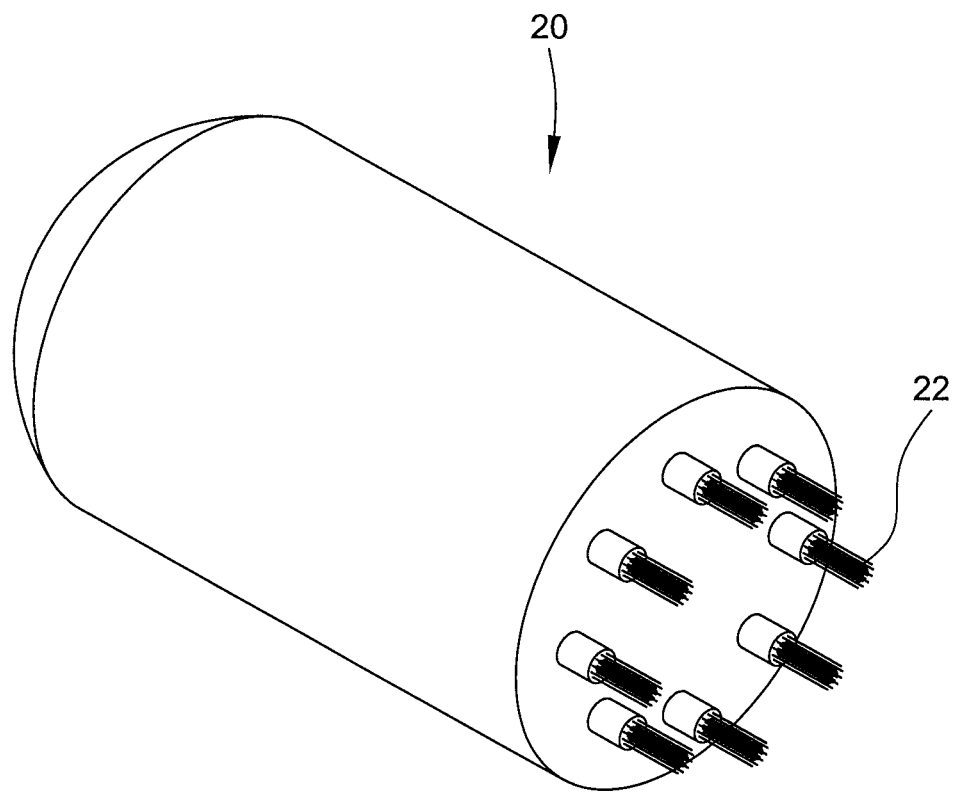
FIG. 2 is a perspective view showing a discharge electrode of the embodiment of the present invention.

Please refer to FIG. 1 to FIG. 4 for an efficient electrostatic particle-into-liquid sampler in accordance with an embodiment of the present invention. The sampler has a main body 10, a discharge electrode 20, a conductive rod 30 and an insulating casing 40.

The main body 10 is made of conductive material such as stainless steel. The main body has an aerosol inlet 11 on a top side, an aerosol outlet 12 on a bottom side, a water outlet 13 on the bottom side, an cylinder wall 14, a plurality of water injecting opening 15 formed on the cylinder wall 14, and a clean air inlet 16 also formed on the cylinder wall 14. To facilitate the installation of the discharge electrode 20 and the conductive rod 30, the cylinder wall 14 can be divided into several assembleable parts. The cylinder wall 14 defines a particle charging area Z1 and a particle collecting area Z2. The particle charging area Z1 is communicated with the aerosol inlet. The particle collecting area Z2 is communicated with and located downstream of the particle charging area Z1. When the sampler is working, the cylinder wall 14 is grounded such that the cylinder wall 14 can have a polarity opposite to that of the discharge electrode 20 and the conductive rod 30. To separately collect gas sample and water sample, the aerosol outlet 12 is not directly communicated with the water outlet 13. Instead, the aerosol outlet 12 and the water outlet 13 are communicated with the particle collecting area Z2 respectively. In the present embodiment, the main body 10 has a gas tube disposed at its bottom end, in which a top end of the gas tube is higher than the water outlet 13, and the aerosol outlet 12 is defined in the gas tube. The water injecting opening 15 and the clean air inlet 16 are both communicated with the particle charging area Z1 to introduce water jet and clean air jet respectively. To increase the flushing efficiency, the water injecting opening 15 and the clean air inlet 16 can be designed to introduce the water jet and the clean air jet in a tangential direction of the cylinder wall 14, such that the introduced water can be formed as a water film on the cylinder wall 14 and spirally flush downward. The water can be injected by syringe pumps. Solenoid valves can be utilized to accumulate water pressure before releasing the water so as to create pulse water flows. In other possible embodiments, there can be only one water injecting opening formed on the cylinder wall.

The discharge electrode 20 is disposed at the center of the particle charging area Z1 and located below the aerosol inlet 11. Because aerosol can be axially introduced into the sampler via the aerosol inlet 11, the aerosol can flow substantially through the particle charging area Z1 and the particle collecting area Z2 in an axial direction. Thus the particles in the aerosol have lower chance to collide the discharge electrode 20 nor attach to locations other than the cylinder wall. In the present embodiment, the discharge electrode 20 has an iron rod 21 and a plurality of carbon fiber brushes 22. The carbon fiber brushes 22 each has a plurality of carbon fiber strips substantially parallel to each other. The carbon fiber brushes 22 electrically connect to the iron rod 21. In the present embodiment, the insulating casing 40 substantially encapsulates the iron rod 21 so that the discharge electrode 20 can be shielded in the air-flowing direction to prevent particles from attaching thereto. The carbon fiber brushes 22 extend downward from the insulating casing 40. The discharge electrode 20 can be applied with high voltage power to create an electric field between the discharge electrode 20 and the cylinder wall 14 in a manner that the discharge electrode 20 can generate corona. Ion cloud can be formed between the carbon fiber brushes 22 and the cylinder wall 14 to ionize the particles passing through the particle charging area Z1. For instance, the particles can be charged with positive ions.

The conductive rod 30 is disposed at the center of the particle collecting area Z2 and located beneath the discharge electrode 20. The conductive rod 30 can also be applied with high voltage power having the same polarity with the charged particles so that the grounded cylinder wall 14 has an opposite polarity to attract and collect the charged particles. The high voltage power applied to the conductive rod 20 is intentionally designed to be insufficient to generate corona. Preferably, the conductive rod 30 has insulators 31, 32 on its top end and its bottom end to mitigate electronic field interference. Insulated supporters can also be utilized to support the discharge electrode 20 and the conductive rod 30 within the main body respectively.

Two power supplies can be used to supply high voltage power to the discharge electrode 20 and the conductive rod 30, respectively. It is noticeable that the voltage applied to the discharge electrode 20 should be higher than its corona inception voltage so that the discharge electrode 20 can discharge corona. The voltage applied to the conductive rod 30 is normally lower than its corona inception voltage to prevent corona.

Figure 3:
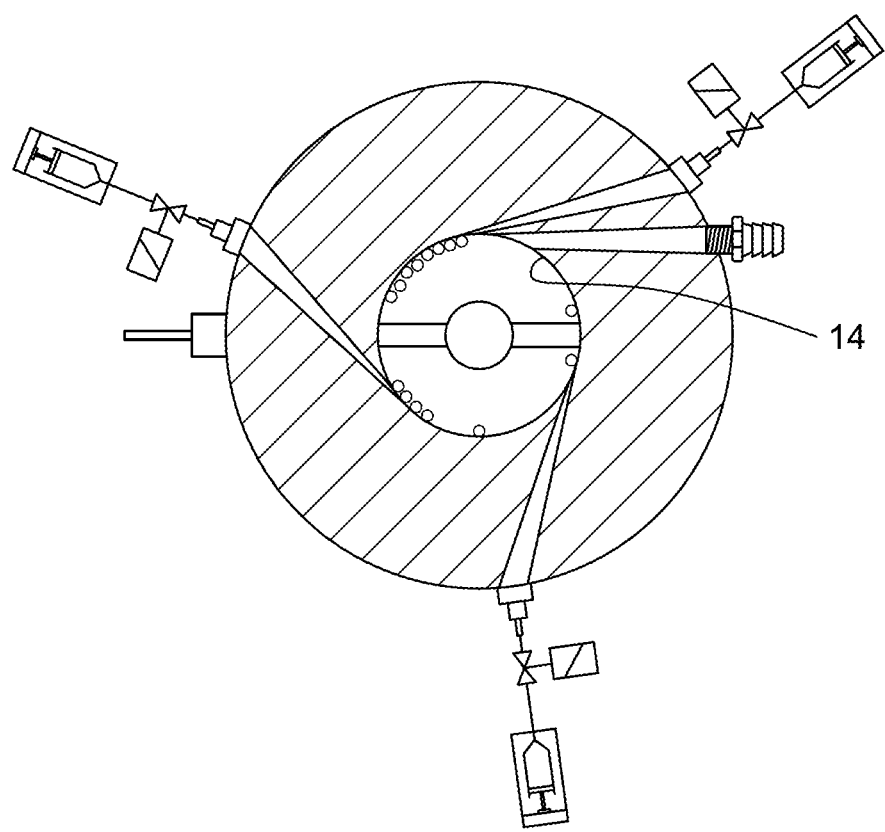
FIG. 3 is a cross section showing the embodiment of the present invention, in which the sampler is working in a dry mold.
Figure 4:
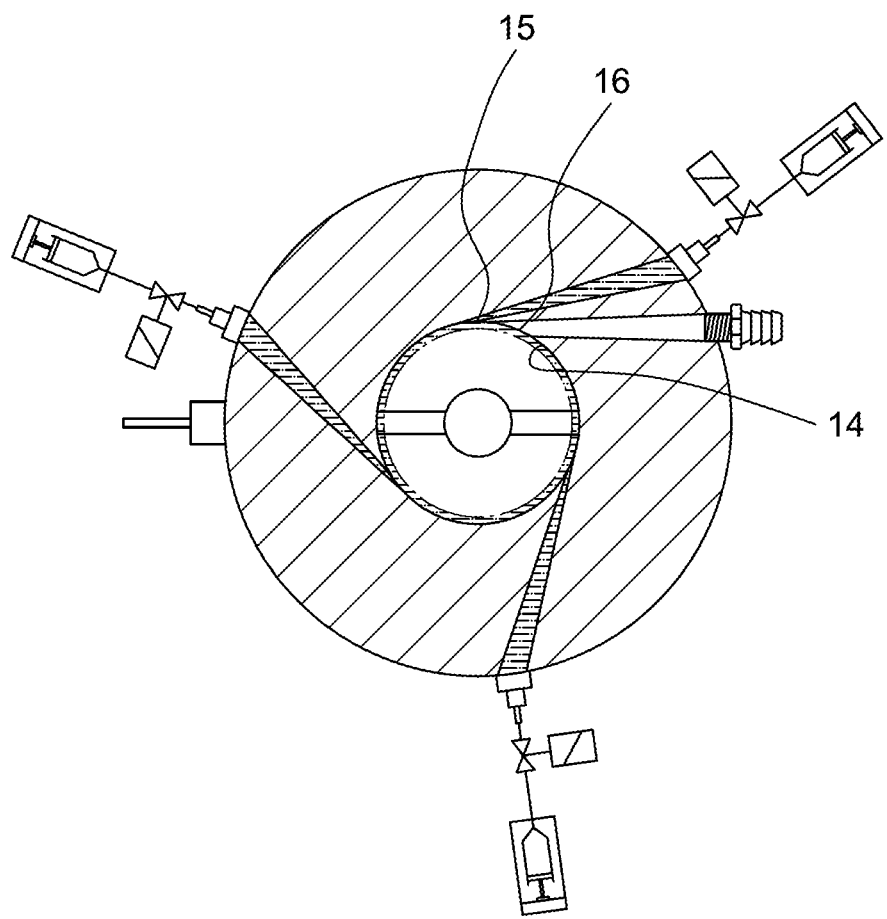
FIG. 4 is a cross section showing the embodiment of the present invention, in which the sampler is working in a wet mold.

As shown in FIG. 3, when the aerosol flows through the particle charging area Z1 and the particle collecting area Z2, the particles in the aerosol can be charged and attach to the cylinder wall 14 with the opposite polarity. After a period of time, high voltage power is no longer applied to the discharge electrode 20 and the conductive rod 30, such that the discharge electrode 20 stops generating corona. As shown in FIG. 4, water can be injected into the main body via the water injecting openings 15 to dislodge the particles deposited on the cylinder wall. The water is then sampled from the water outlet 13 for later analysis.

To reduce the generation of ozone, the voltage applied to the discharge electrode 20 should not be too high. Within tolerable sampling error range, the ozone generated when the discharge electrode 20 and the conductive rod 30 are working should be less than 100 ppb so as to reduce the generation of $NH_4^+$ and $NO_3^-$. In an experiment, the discharge electrode 20 is working at 4000 V and the conductive rod 30 is working at 5000 V. The generated ozone is 70-90 ppb. Collection efficiency for nano particles can reach 92.4-98.6%. $NH_4^+$ and $NO_3^-$ are generated at concentrations of $4.2\pm1.65$ $\mu g/m^3$ and $2.6\pm0.78$ $\mu g/m^3$ respectively. Another sampler which is fabricated based on the design disclosed on FIG. 10 of U.S. Pat. No. 9,671,320 is also tested as a control group. To achieve similar collection efficiency, i.e. 92-100%, the discharge electrode of the control group should be applied with 9000 V power. As a result, $NH_4^+$ and $NO_3^-$ are generated at 46.8 and 143.7 $\mu g/m^3$ in the control group. Sampling artifacts are thus significantly increased.

In another experiment for iron recovery rate, nonvolatile particles of $Na_2SO_4$ and $(NH_4)_2SO_4$ and volatile particles of $NH_4NO_3$ are used. 1% (v/v) aqueous solutions are prepared using the afore-mentioned particles respectively. These solutions are then atomized by Atomizer Model 3076, TSI. The aerosol are then dried and static neutralized before entering the electrical classifier to prepare particles with single diameter of 70, 90, 110, 130 and 150 nm respectively. These particles are then introduced into a static neutralizer and thereafter divided into two flows which are introduced simultaneously into the sampler of the afore-mentioned embodiment and a Scanning Mobility Particle Sizer, TSI, Model 3934, respectively. Particles are thus sampled. Number concentrations obtained by the SMPS are then converted into mass concentration based on densities of different tested particles. The sample obtained by the sampler is analyzed by ion chromatography can compared with the result of the SMPS. Ion recovery rate for different ions are calculated. It is observed that the ion recovery rate for $Na_2SO_4$, $(NH_4)_2SO_4$ and $NH_4NO_3$ are very high when using the sampler of the above mentioned embodiment. The recovery rate of $Na^+$ and $SO_4^{2-}$ can reach $93\pm10\%$ ($R^2=0.98$) and $88\pm4.5\%$ ($R^2=0.99$) respectively. The recovery rate of $NH_4^+$ and $SO_4^{2-}$ can reach $105\pm18\%$ ($R^2=0.98$) and $92\pm5.6\%$ ($R^2=0.98$) respectively. The recovery rate of $NH_4^+$ and $NO_3^-$ can reach $103\pm15\%$ ($R^2=0.92$) and $96\pm8\%$ ($R^2=0.97$) respectively.

Compared the sampler of the present invention with the conventional PILS, the accuracy and correlation ration of the present invention are outstanding. This is so because PILS mixes aerosol with high temperature vapor during condensation, so that the surface temperature of the particles increases. Besides, their aqueous solutions are acidic with pH of 5.6, which causes 12-16% of $NH_4^+$ evaporation (Sorooshian et al., 2006, Li et al., 2017). When the concentration of $NO_3^-$ is lower than 2 μg/m³, $NO_3^-$ becomes sticky and attach to the tube surface. The accuracy of PILS is thus reduced (Orsini et al., 2003). On the contrary, the sampler of the present invention utilizes electrostatic to collect particles. $NH_4^+$ evaporation caused by high temperature can be prevented. The result shows the error for $NH_4^+$ is lower than 10%. In addition, the particle loss of the sampler of the present invention is relatively low (less than 5% particle loss for particles with diameter of 14 nm-4 μm). Sticky particles can thus be effectively collected. It is verified that the accuracy and the correlation ration for low concentration $NO_3^-$ is more superior to PILS.

What is claimed is:

1. An efficient electrostatic particle-into-liquid sampler, comprising:
   a main body, having an aerosol inlet on a top side, an aerosol outlet on a bottom side, a water outlet on the bottom side, a cylinder wall and at least one water injecting opening formed on the cylinder wall, the cylinder wall defining a particle charging area communicating with the aerosol inlet, the cylinder wall defining a particle collecting area communicating with the aerosol outlet, the water injecting opening being communicated with the particle charging area, the particle collecting area being communicated with and located downstream of the particle charging area, the cylinder wall being made of conductive material;
   a discharge electrode, disposed in the particle charging area and located below the aerosol inlet, the discharge electrode having at least one carbon fiber brush for corona discharge, the carbon fiber brush having a plurality of carbon fiber strips;
   a conductive rod, disposed in the particle collecting area for forming an electric field between the conductive rod and the cylinder wall in a manner that at least a part of charged particles could attach to the cylinder wall;
   wherein the water injecting opening is adapted to, after the discharge electrode stops corona discharging, inject deionized water in the main body to dislodge the particles attached on the cylinder wall, the water outlet is adapted to sample the water;
   wherein ozone generated when the discharge electrode and the conductive rod are working is lower than 100 ppb.

2. The efficient electrostatic particle-into-liquid sampler of claim 1, wherein the main body further has a clean air inlet formed on the cylinder wall and communicated with the particle charging area, the clean air inlet is adapted to, when the water injecting opening injects the water, introduce clean air jet into the main body in a manner that a water film is formed and spirally flows downward on the cylinder wall.

3. The efficient electrostatic particle-into-liquid sampler of claim 2, wherein the water injecting opening is adapted to inject the deionized water in a tangential direction of the cylinder wall; the clean air inlet is adapted to introduce the clean air jet in another tangential direction of the cylinder wall.

4. The efficient electrostatic particle-into-liquid sampler of claim 1, wherein the water injecting opening is adapted to introduce the deionized water in a pulsation manner by opening and closing solenoid valves intermittently.

5. The efficient electrostatic particle-into-liquid sampler of claim 1, wherein a top end and a bottom end of the conductive rod are shielded by an insulator, respectively.

6. The efficient electrostatic particle-into-liquid sampler of claim 1, further comprising an insulating casing encapsulating a part of the discharge electrode, the carbon fiber brush axially extending downward from a bottom of the insulating casing.

* * * * *